United States Patent
Raines

(10) Patent No.: US 11,904,159 B2
(45) Date of Patent: Feb. 20, 2024

(54) IMPLANTABLE STIMULATION LEAD INCLUDING A COILED LEAD BODY AND METHODS FOR FORMING THE SAME

(71) Applicant: Advanced Neuromodulation Systems, Inc., Plano, TX (US)

(72) Inventor: Aaron Raines, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 5 days.

(21) Appl. No.: 17/008,058

(22) Filed: Aug. 31, 2020

(65) Prior Publication Data
US 2022/0062624 A1   Mar. 3, 2022

(51) Int. Cl.
A61N 1/05 (2006.01)
H01B 13/008 (2006.01)
H01B 13/00 (2006.01)
A61B 18/14 (2006.01)

(52) U.S. Cl.
CPC .............. *A61N 1/05* (2013.01); *H01B 13/008* (2013.01); *H01B 13/0016* (2013.01); *A61B 18/1492* (2013.01); *A61N 1/056* (2013.01); *A61N 1/0551* (2013.01)

(58) Field of Classification Search
CPC ........ A61N 1/05; A61N 1/056; A61N 1/0587; H01B 13/0016; H01B 13/008; A61B 18/1492

See application file for complete search history.

(56) References Cited

U.S. PATENT DOCUMENTS

| | | | | |
|---|---|---|---|---|
| 5,372,138 A * | 12/1994 | Crowley | ............ | A61B 18/1492 600/463 |
| 5,437,282 A * | 8/1995 | Koger | ............... | A61M 25/0045 600/463 |
| 5,845,396 A * | 12/1998 | Altman | ................ | H01B 13/008 607/116 |
| 6,477,427 B1 | 11/2002 | Stolz et al. | | |
| 7,519,432 B2 | 4/2009 | Bolea | | |
| 7,555,349 B2 | 6/2009 | Wessman et al. | | |
| 8,484,841 B1 | 7/2013 | Burros et al. | | |
| 9,844,661 B2 | 12/2017 | Franz et al. | | |
| 2002/0143377 A1* | 10/2002 | Wessman | ................. | A61N 1/05 607/116 |
| 2003/0105505 A1* | 6/2003 | Pianca | ..................... | A61N 1/05 607/122 |

(Continued)

*Primary Examiner* — Pamela M. Bays
(74) *Attorney, Agent, or Firm* — Armstrong Teasdale LLP

(57) ABSTRACT

A method of forming a stimulation lead includes forming an implantable lead body, including helically winding at least one cable about a mandrel to form a coiled cable assembly in a first, restrained state. Helically winding the at least one cable includes applying a tensile force to the at least one cable as the at least one cable is wound about the mandrel. Forming the lead body also includes releasing the tensile force from the at least one cable to allow the coiled cable assembly to release stored mechanical energy and transition from the restrained state to a second, relaxed state in which the coiled cable assembly is substantially free of stored mechanical energy. The method further includes subjecting the lead body to a reflow process by applying heat to the lead body, where the tensile force is released prior to the lead body being subjected to the reflow process.

14 Claims, 14 Drawing Sheets

(56) References Cited

U.S. PATENT DOCUMENTS

| | | | |
|---|---|---|---|
| 2005/0027340 A1* | 2/2005 | Schrom | A61N 1/05 607/116 |
| 2006/0107644 A1* | 5/2006 | Dye | A61N 1/05 57/13 |
| 2006/0111768 A1 | 5/2006 | Wessman et al. | |
| 2010/0179630 A1* | 7/2010 | Williams | A61N 1/05 607/122 |
| 2014/0005599 A1* | 1/2014 | Sage | A61N 1/3605 604/93.01 |
| 2014/0031911 A1* | 1/2014 | Williams | A61N 1/05 156/51 |
| 2017/0080213 A1 | 3/2017 | Wright et al. | |

* cited by examiner

2000

2002 — HELICALLY WIND AT LEAST ONE CABLE ABOUT A MANDREL TO FORM A COILED CABLE ASSEMBLY BY APPLYING A TENSILE FORCE TO THE AT LEAST ONE CABLE AS THE AT LEAST ONE CABLE IS WOUND ABOUT THE MANDREL

2004 — REMOVE THE MANDREL FROM THE COILED CABLE ASSEMBLY SUBSEQUENT TO THE AT LEAST ONE CABLE BEING HELICALLY WOUND ABOUT THE MANDREL

2006 — POSITION THE COILED CABLE ASSEMBLY WITHIN AN OUTER LUMEN OF AN OUTER SHEATH

2008 — RELEASE THE TENSILE FORCE FROM THE AT LEAST ONE CABLE TO ALLOW THE COILED CABLE ASSEMBLY TO RELEASE STORED MECHANICAL ENERGY AND TRANSITION FROM A FIRST, RESTRAINED STATE TO A SECOND, RELAXED STATE IN WHICH THE COILED CABLE ASSEMBLY IS SUBSTANTIALLY FREE OF STORED MECHANICAL ENERGY

2010 — POSITION AN INNER SHEATH WITHIN A COIL PASSAGE DEFINED BY THE COILED CABLE ASSEMBLY

2012 — SUBJECT THE LEAD BODY TO A REFLOW PROCESS

FIG. 20

IMPLANTABLE STIMULATION LEAD INCLUDING A COILED LEAD BODY AND METHODS FOR FORMING THE SAME

BACKGROUND OF THE DISCLOSURE

A. Field of the Disclosure

The present disclosure relates generally to lead assemblies for stimulation systems. In particular, the present disclosure relates to methods of forming a coil lead body for a stimulation lead of a stimulation system.

B. Background Art

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors in addition to relieving symptoms of failed back surgery syndrome (FBSS) and complex regional pain syndrome (CRPS). Types of neurostimulation include deep brain stimulation (DBS), spinal cord stimulation (SCS) for the treatment of chronic pain and similar disorders, and Dorsal Root Ganglion (DRG) stimulation. In DBS, pulses of electrical current are delivered to target regions of a subject's brain, for example, for the treatment of movement and effective disorders such as PD and essential tremor.

Neurostimulation systems typically include an implantable pulse generator (IPG) and one or more stimulation leads. Neurostimulation systems are devices that generate electrical pulses and deliver the pulses to nervous tissue of a patient to treat a variety of disorders, such as those described above. A stimulation lead includes a lead body of insulative material that encloses wire conductors. The distal end of the stimulation lead includes multiple electrodes, or contacts, that impinge upon patient tissue and are electrically coupled to the wire conductors. The proximal end of the lead body includes multiple terminals (also electrically coupled to the wire conductors) that are adapted to receive electrical pulses.

In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The IPG is typically implanted in the patient within a subcutaneous pocket created during the implantation procedure.

The IPG is typically implemented using a metallic housing (or can) that encloses circuitry for generating the electrical stimulation pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

A stimulation lead includes a lead body. One known method of forming a lead body is a continuous process in which lead bodies are rolled onto reels. Discrete lengths are subsequently cut from the reels, and ends are terminated with contacts (e.g., terminals) and electrodes. In the continuous process, a cable (or wire) is directly wound about an inner sheath, and the cable and inner sheath are encapsulated in a polymer tube. The continuous process of forming lead bodies, however, presents several challenges in assembling a stimulation lead. For example, when heat is applied to the polymer tube (e.g., to expose underlying conductive wires), the enclosed cable has a tendency to unwind and expand out of the softened polymer tube as a result of pent up energy (e.g., spring energy) stored within the wound cable. This makes it difficult to contain the wound cable within the polymer tube, and to finish the ends of the lead body, for example, by electrically connecting contacts (e.g., leads and terminals) to the conductive wire within the polymer tube.

SUMMARY OF THE DISCLOSURE

The present disclosure is directed to a method of forming a stimulation lead. The method includes forming an implantable lead body. Forming the implantable lead body includes helically winding at least one cable about a mandrel to form a coiled cable assembly in a first, restrained state. Helically winding the at least one cable includes applying a tensile force to the at least one cable as the at least one cable is wound about the mandrel. Forming the implantable lead body also includes releasing the tensile force from the at least one cable to allow the coiled cable assembly to release stored mechanical energy and transition from the restrained state to a second, relaxed state in which the coiled cable assembly is substantially free of stored mechanical energy. The method further includes subjecting the lead body to a reflow process by applying heat to the lead body, where the tensile force is released prior to the lead body being subjected to the reflow process.

The present disclosure is further directed to a stimulation lead including an implantable lead body, a plurality of terminals located at a proximal end of the lead body, and a plurality of electrodes located at a distal end of the lead body. The lead body includes a coiled cable assembly including at least one cable helically wound about a central longitudinal axis of the lead body. The coiled cable assembly is substantially free of stored mechanical energy. Each of the plurality of terminals is electrically coupled to at least one of the plurality of electrodes through the coiled cable assembly The present disclosure is further directed to a stimulation system including an implantable pulse generator (IPG) and a stimulation lead connected to the IPG. The stimulation lead includes an implantable lead body that includes a coiled cable assembly enclosed within an outer polymeric sheath. The coiled cable assembly includes a plurality of cables helically wound about a central longitudinal axis of the lead body, where each cable includes a plurality of conductive wires. The stimulation lead further includes a plurality of terminals located at a proximal end of the lead body, and a plurality of electrodes located at a distal end of the lead body, where each of the plurality of terminals is electrically coupled to at least one of the plurality of electrodes through the coiled cable assembly. The coiled cable assembly is substantially free of stored mechanical energy.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 20 is a flow diagram of an exemplary method of forming a lead body for use in a stimulation lead.

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, the present disclosure is directed to lead bodies for stimulation leads of stimulation systems, for use in medical procedures such as tissue stimulation, and methods of forming the lead bodies.

The embodiments described herein include helically winding at least one cable about a mandrel to form a coiled cable assembly. In particular, during the helical winding process, a tensile force is applied to the cable as it is wound about the mandrel so that the cable conforms to the shape of the mandrel and helical windings are imparted to the shape of the cable. Mechanical or spring energy is stored in the cable as it is wound about the mandrel. The coiled cable assembly is therefore in a stored-energy or restrained state immediately following the helical winding process. The embodiments described herein include allowing the stored mechanical energy within the coiled cable assembly to dissipate or be released, for example, by releasing the tensile force from the cable after the helical winding process. Releasing the tensile force enables the coiled cable to relax and expand, thereby releasing the energy stored within the coiled cable. Thus, the coiled cable transitions from the restrained state to an expanded state. In the expanded state, the coiled cable is in a final, "free" state because the coiled cable no longer has stored spring energy, and therefore does not have a tendency to unwind and expand. This coil (e.g., the coiled cable assembly) is assembled with other components, such as the outer sheath and inner sheath, to form the lead body.

The disclosed embodiments provide an efficient method of forming lead bodies as compared to at least some known methods, such as the continuous lead body process. The embodiments described herein address the difficulties described above, and improve upon the continuous lead body process by (i) forming each component of the lead body as a separate item, including a coiled conductor (e.g., a coiled cable), and (ii) assembling the individual components together. In particular, by forming the coil conductor separately from the other components of the lead body, the methods described herein enable the coil conductor to be free of inherent "pent up" mechanical energy that would otherwise be stored within the coil conductor as a result of helically winding the conductor. Thus, when heat is applied to the polymer of the lead body, the coil conductor retains its size and shape, rather than expanding.

Figure 1:
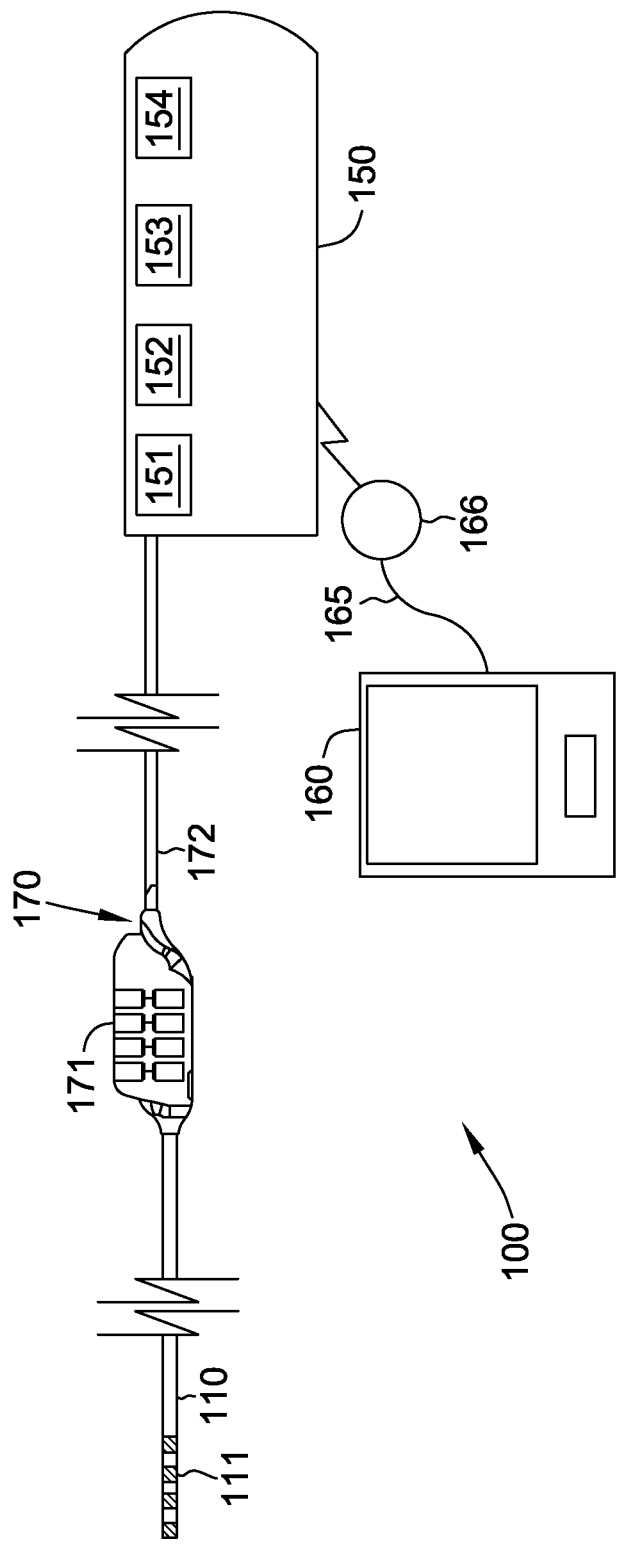
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

Components suitable for use as and/or within IPG 150, such as a processor and associated charge control circuitry, are described, for example, in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body (e.g., lead body 202, shown in FIG. 2) of insulative material about a plurality of conductors within the material that extend from a proximal end of lead 110 to its distal end. The conductors electrically couple a plurality of electrodes 111 to a plurality of terminals (not shown in FIG. 1) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

A controller device 160 may be implemented to recharge battery 153 of IPG 150 (although a separate recharging device could alternatively be employed). A "wand" 165 may be electrically connected to controller device 160 through suitable electrical connectors (not shown). The electrical connectors are electrically connected to a coil 166 (the "primary" coil) at the distal end of wand 165 through respective wires (not shown). Controller device 160 generates an AC-signal to drive current through coil 166 of wand 165. When primary coil 166 and secondary coil are suitably positioned relative to each other (e.g., when primary coil 166 is placed against the patient's body immediately above the secondary coil (not shown), the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150.

External controller device 160 is also a device that permits the operations of IPG 150 to be controlled (e.g., by a user) after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The embodiments described herein may be implemented within both SCS and DBS stimulation systems.

Figure 2:
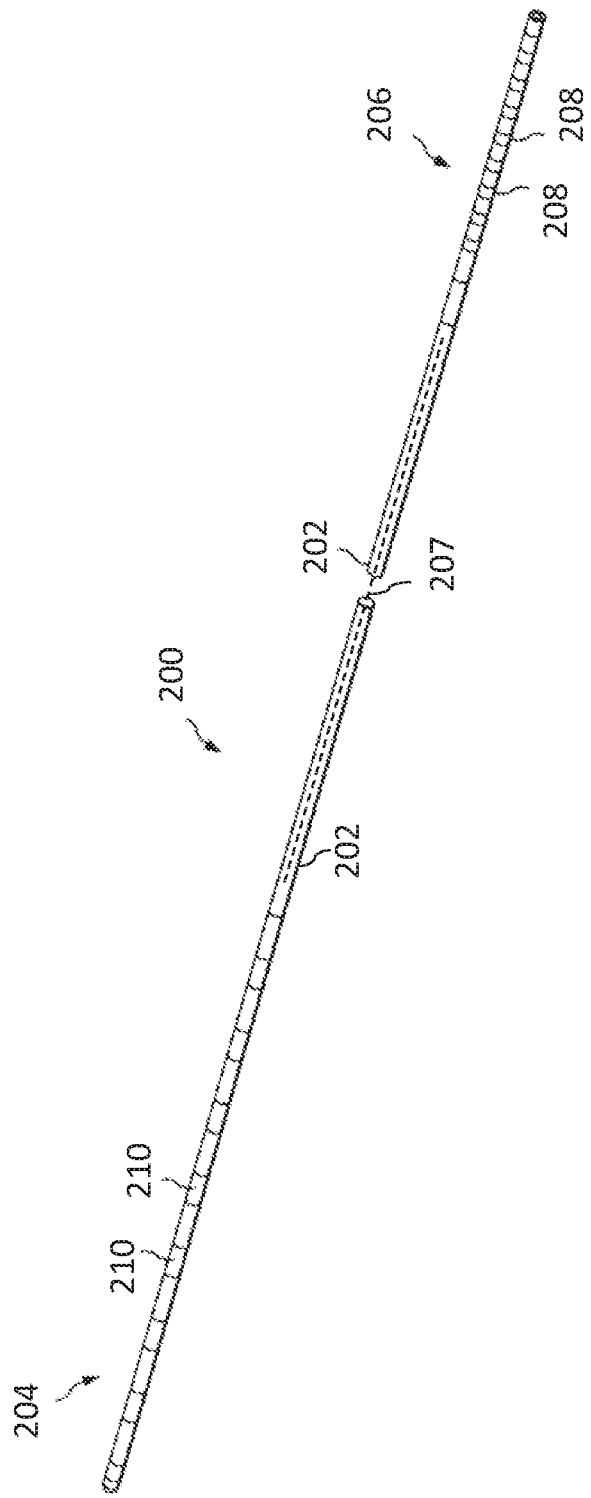
FIG. 2 is a perspective view of an exemplary lead body suitable for use in the system shown in FIG. 1.

FIG. 2 illustrates an exemplary stimulation lead 200 suitable for use in system 100 (shown in FIG. 1). Lead 200 includes an elongated lead body 202 which includes a distal end portion 204 and a proximal end portion 206. Lead body 202 has a length that extends along a longitudinal axis 207 between the distal and proximal end portions 204 and 206. The term longitudinal axis encompasses both linear and non-linear axes. The longitudinal axis of the lead body 202 extends along a curved path that changes as lead body 202 is flexed, bent and otherwise manipulated. Lead body 202 includes an insulating sheath of a suitable insulative, biocompatible, biostable material such as, for example, PEEK (i.e. Polyetheretherketones), silicone rubber or polyurethane, extending substantially the entire length of the lead body 202.

In one embodiment, lead body 202 is formed from a medical grade, substantially inert material, for example, polyurethane, silicone, or the like. In an example embodiment, lead body 202 is formed from a material that is non-reactive to the environment of the human body, provides a flexible and durable (i.e., fatigue resistant) exterior structure for the components of lead 200, and insulates adjacent terminals 208 and/or electrodes 210.

In the illustrated embodiment, a plurality of electrically conductive terminals (e.g., electrical terminals) 208 is provided at proximal end portion 206 of lead body 202. Terminals 208 are configured to be connected to respective electrical conductors, such as a plurality of wires, within lead 200. Lead 200 also includes a plurality of electrically conductive electrodes 210 provided at distal end portion 204 of lead body 202. In an example embodiment, terminals 208 and electrodes 210 are formed of a non-corrosive, highly conductive material. Examples of such material include stainless steel, MP35N, platinum, and platinum alloys. In another embodiment, terminals 208 and electrodes 210 are formed of a platinum-iridium alloy. Lead 200 may include any suitable number of terminals 208 and electrodes 210 that enables system 100 to function as described herein.

Lead body 202 provides an enclosure for conductors that connect terminals 208 with one or more electrodes 210. Conductors are formed of a conductive material that exhibits the desired mechanical properties of low resistance, corrosion resistance, flexibility, and strength. Examples of suitable conductors include a stranded wire and a coiled wire. It should be appreciated that in the context of lead 200, conductors are required to fit within the interior of lead body 202. In an exemplary embodiment, a plurality of cables 402 (shown in FIG. 4) is wound to form a coiled cable assembly, such as, for example, coiled cable assembly 312 (shown in FIG. 3). Each cable in the coiled cable assembly may be coated with an insulative material to protect the cable if body 202 were breached during use.

Figure 3:
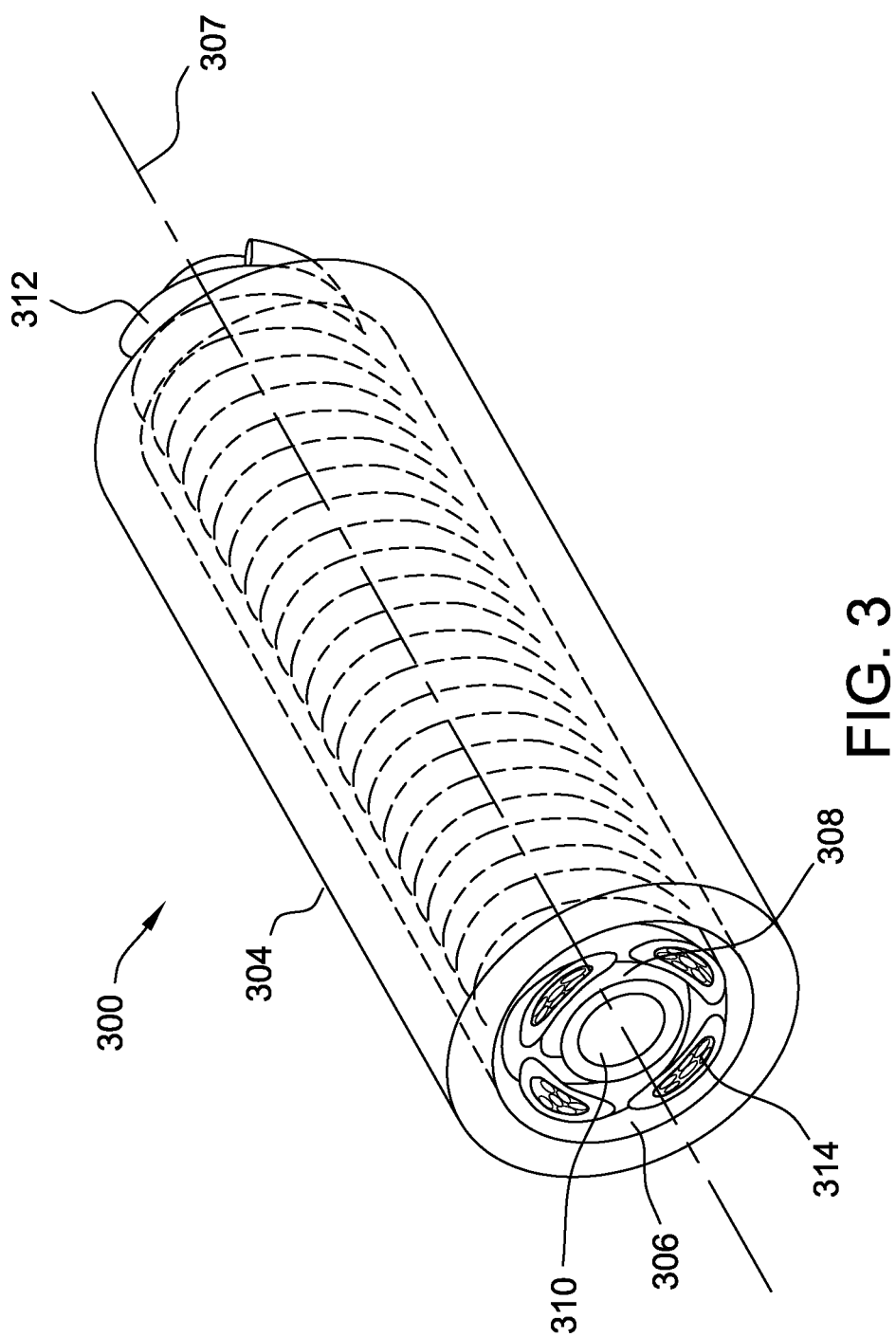
FIG. 3 is a perspective view of an exemplary assembled lead body.

FIG. 3 is a perspective view of an exemplary assembled lead body 300 prior to applying a reflow process. As described below, a reflow process is applied to assembled lead body 300 to form a reflowed lead body 1200 (shown in FIG. 14) suitable for use in the stimulation leads described herein (e.g., stimulation leads 110, 200). Reflowed lead body 1200 may be substantially similar to or the same as lead body 202.

As shown in FIG. 3, assembled lead body 300 includes an outer sheath 304 defining an outer lumen 306 extending along the length of lead body 300. Lead body 300 also includes an inner sheath 308 defining an inner lumen 310 extending along the length of assembled lead body 300. Assembled lead body 300 has a length that extends along a longitudinal axis 307 of lead body 300. A diameter of inner lumen 310 (e.g., $ID_{IS}$, shown in FIG. 13) is smaller than a diameter of outer lumen 306 (e.g., $D_{OL}$, shown in FIG. 12). Lead body 300 also includes a coiled cable assembly 312. Coiled cable assembly 312 comprises multiple, separate cables 402 (shown in FIG. 4) wound within lead body 300. Each cable 402 includes a plurality of conductive wires 314.

Figure 4:
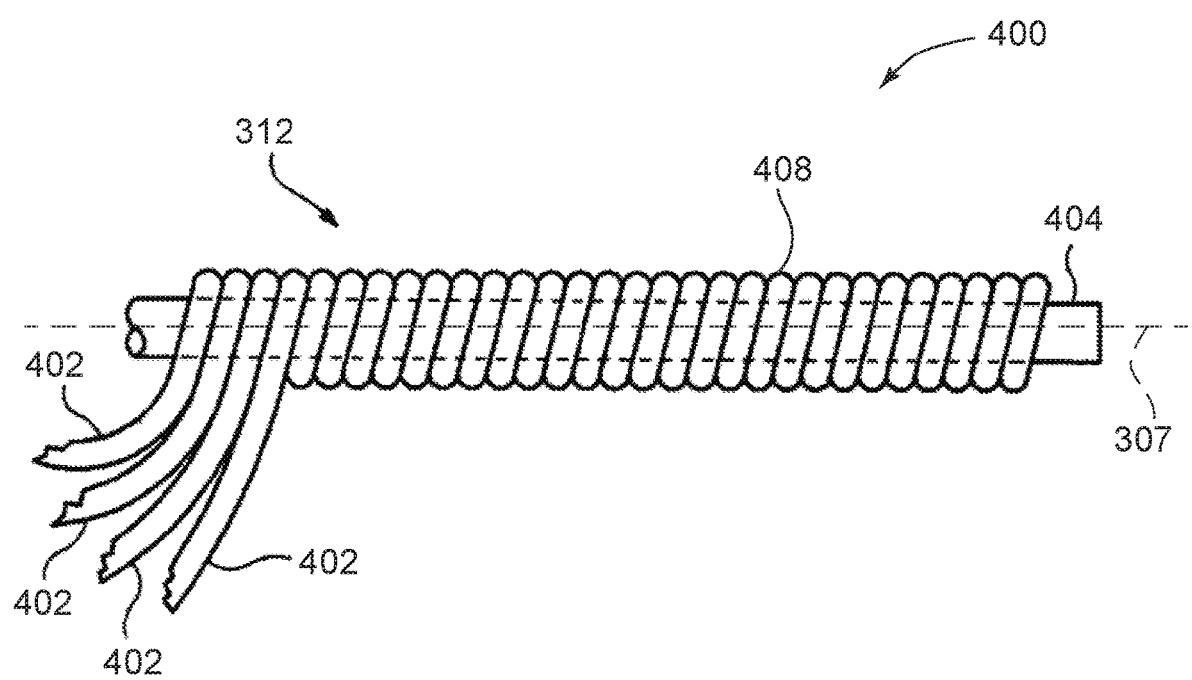
FIG. 4 illustrates a step in an exemplary method of forming the assembled lead body of FIG. 3.

FIG. 4 illustrates a step 400 in an exemplary method of forming assembled lead body 300 (shown in FIG. 3). The exemplary method of forming assembled lead body 300 described herein refers to steps prior to applying a reflow process, as described below with reference to FIGS. 14 and 15. In particular, the exemplary method of forming assembled lead body 300 includes forming coiled cable assembly 312 (shown in FIG. 3), and subsequently assembling the separate components of lead body 300 together.

Figure 5:
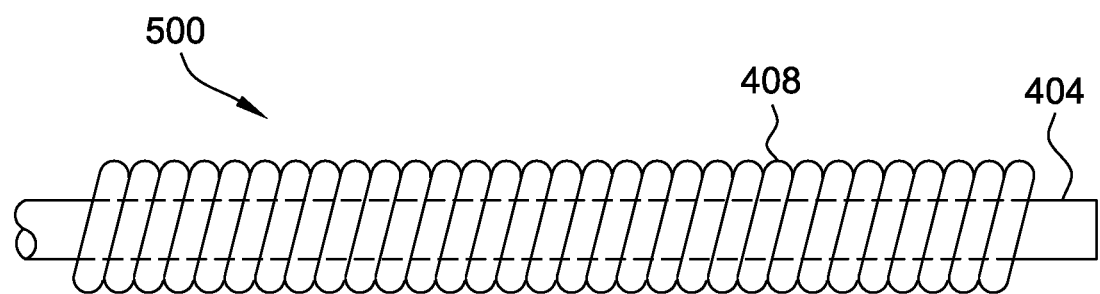
FIG. 5 is a side view of an exemplary coil arrangement that can be formed in the step shown in FIG. 4.
Figure 6:
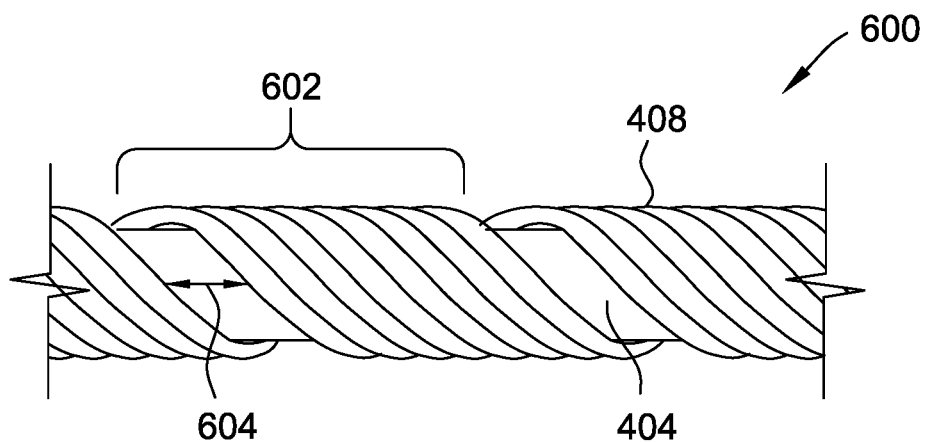
FIG. 6 is a side view of another exemplary coil arrangement that can be formed in the step shown in FIG. 4.

FIG. 4 illustrates a plurality of cables 402 and a mandrel 404 extending along the longitudinal axis 307. Each cable 402 includes a plurality of individual wires (e.g., conductive wires 314, shown in FIG. 3). Step 400 includes helically winding cables 402 about mandrel 404 in a uniform direction, such as in a clockwise direction to form a coiled cable assembly 312. Mandrel 404 is separate and distinct from inner sheath 308 (shown in FIG. 3). Specifically, in step 400, cables 402 are not wound about inner sheath 308, but instead are wound around mandrel 404, which is not a component of assembled lead body 300. Coiled cable assembly 312 is formed by helically winding cables 402 about mandrel 404 to form a plurality of concentric loops 408. In particular, during the helical winding process, a tensile force is applied to cables 402 (e.g., to one or both ends of cables 402) as loops 408 are wound about mandrel 404. FIGS. 5 and 6 illustrate exemplary coil arrangements 500, 600 that can be formed in step 400 by winding cables 402 about mandrel 404. In FIG. 5, coil arrangement 500 includes a plurality of concentric loops 408 that are closely spaced together. Cables 402 may be helically wound about mandrel 404 such that each loop 408 is in contact with adjacent loops 408. In FIG. 6, coil arrangement 600 includes groups 602 of closely spaced loops 408 that are separated by a distance 604 that is larger than the spacing between adjacent loops 408 within each group 602. Cables 402 may be helically wound about mandrel 404 such that each group 602 of loops 408 is spaced apart from adjacent groups 602 of loops 408.

Each cable 402 may include one or more layers of insulation. In one embodiment, each cable 402 includes an inner thin layer of perfluoroalkoxy (PFA) and an outer thicker layer of a thermoplastic silicone polycarbonate urethane (e.g., CARBOSIL™). In some embodiments, additional layers of cables 402 may be wound over an initial layer of cables 402 to form a multi-layered coil. In one embodiment, mandrel 404 is formed from a polytetrafluoroethylene (PTFE) coated stainless steel material.

Figure 7:
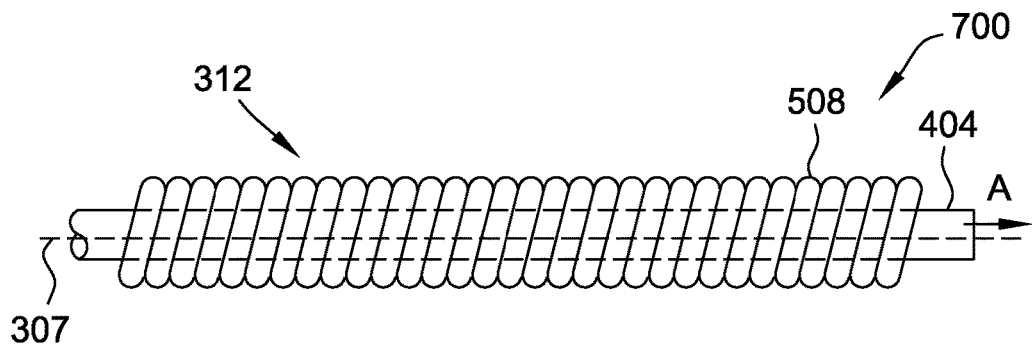
FIG. 7 illustrates another, subsequent step in the exemplary method of forming the assembled lead body of FIG. 3.

FIG. 7 illustrates another, subsequent step 700 in the exemplary method of forming assembled lead body 300 (shown in FIG. 3). In particular, step 700 is another, subsequent step in forming coiled cable assembly 312 (shown in FIG. 3). Step 700 includes removing mandrel 404 from coiled cable assembly 312. Mandrel 404 is slidably removed from coiled cable assembly 312 in the illustrated embodiment, as depicted by arrow A in FIG. 7. Although FIG. 7 illustrates laterally removing mandrel 404 in the direction of arrow A, mandrel 404 may be laterally removed in either direction along the longitudinal axis 307. In some embodiments, a coating may be applied to mandrel 404, such as a PTFE coating, to facilitate the removal of mandrel 404 from coiled cable assembly 312.

Figure 8:
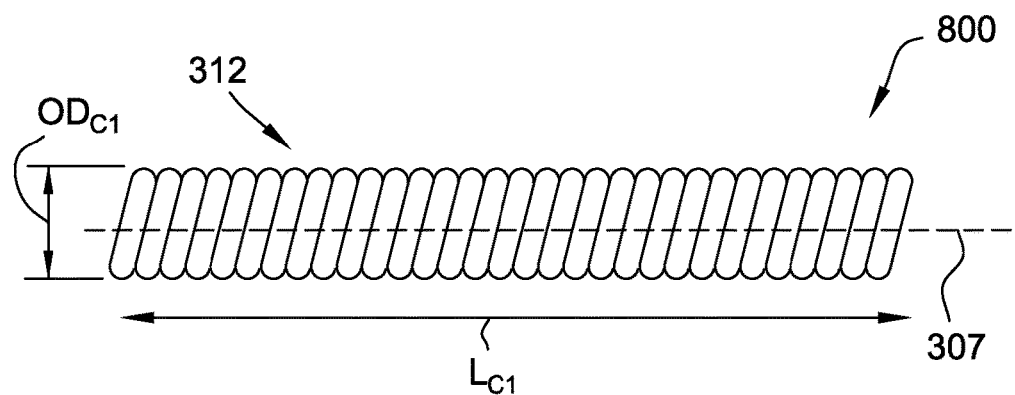
FIG. 8 is a side view of an exemplary coil in a restrained state.

FIG. 8 is a side view of coiled cable assembly 312 in a restrained configuration or state 800 (e.g., first state) with mandrel 404 removed. In the restrained state 800, coiled cable assembly 312 is held under tension (e.g., from the tensile force applied to ends of cables 402 during the helical winding process), and has stored mechanical energy resulting from helically winding cables 402 about mandrel 404 during the helical winding process. The coiled cable assembly 312 may be held in the restrained state 800, for example, by restraining each end of the coiled cable assembly 312 relative to one another. The stored mechanical energy in coiled cable assembly 312 tends to bias coiled cable assembly 312 to an expanded or unwound state. In an example embodiment, coiled cable assembly 312 acts like a wound up spring that stores mechanical energy due to the tensile force applied to cables 402 during the helical winding process. As shown in FIG. 8, coiled cable assembly 312 includes an outer diameter $OD_{C1}$ and a coil length $L_{C1}$ in restrained state 800.

Figure 9:
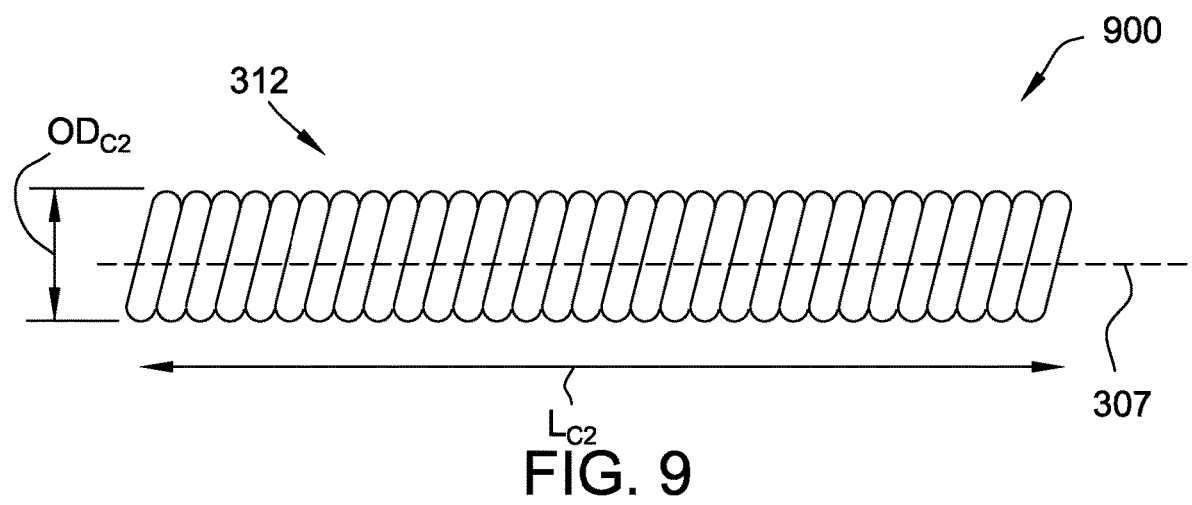
FIG. 9 is a side view of the exemplary coil of FIG. 8 in an expanded state.

FIG. 9 is a side view of coiled cable assembly 312 in a second, expanded state 900, also referred to as a relaxed or free state. The release of the tensile force applied to cables 402 during the helical winding process enables coiled cable assembly 312 to transition from restrained state 800 to expanded state 900, as coiled cable assembly 312 releases stored mechanical energy. In expanded state 900, the outer diameter of coiled cable assembly 312 increases from $OD_{C1}$ (in restrained state 800) to $OD_{C2}$. Similarly, the length of coiled cable assembly 312 increases from $L_{C1}$ (in restrained state 800) to $L_{C2}$. With the release of the tensile force, coiled cable assembly 312 relaxes and expands into expanded state 900, which is a final, stable state (e.g., a free energy state) where coiled cable assembly 312 is free or substantially free of stored mechanical (e.g., torsional) energy. In other words, in expanded state 900, coiled cable assembly 312 no longer has a tendency to unwind or expand, in the absence of an applied force, due to stored mechanical energy. In this sense, the mechanical energy of coiled cable assembly 312 can be modeled as a torsion spring. More specifically, coiled cable assembly 312 behaves like a torsion spring under load, having stored torsional energy, prior to release of the tensile force. After the tensile force is released and coiled cable assembly 312 is allowed to relax, coiled cable assembly 312 behaves like a torsion spring under no load, being free or substantially free of torsional energy.

Figure 10:
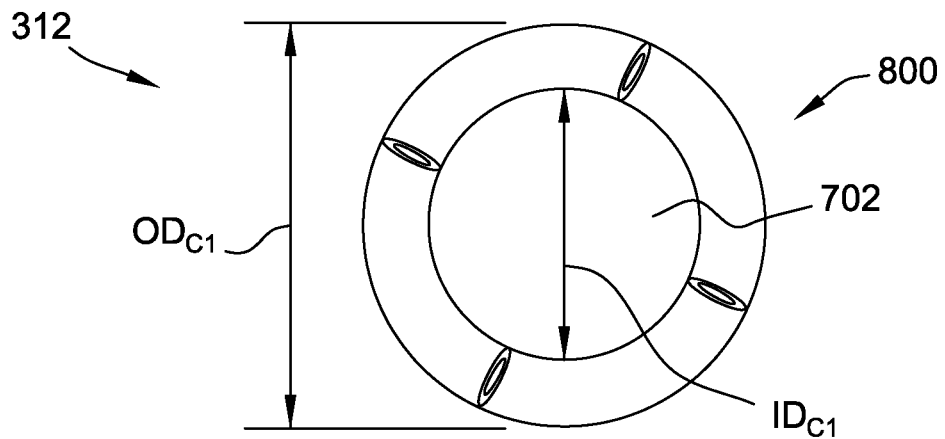
FIG. 10 is an end view of the exemplary coil of FIG. 8 in the restrained state.
Figure 11:
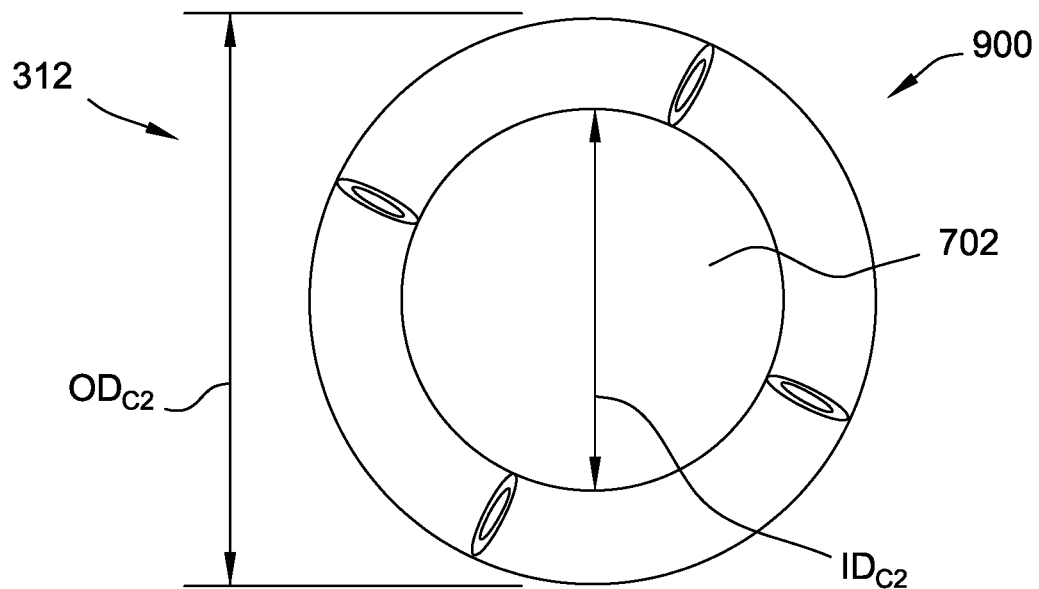
FIG. 11 is an end view of the exemplary coil of FIG. 9 in the expanded state.

FIG. 10 is an end view of coiled cable assembly 312 in restrained state 800. FIG. 11 is an end view of coiled cable assembly 312 in expanded state 900. With reference to FIGS. 8-11, coiled cable assembly 312 defines a central elongate passage 702, which extends along a length of coiled cable assembly 312 along longitudinal axis 307. As shown in FIG. 10, in restrained state 800, coiled cable assembly 312 has an outer diameter $OD_{C1}$ and an inner diameter $ID_{C1}$. As shown in FIG. 11, in expanded state 900, coiled cable assembly 312 has an outer diameter $OD_{C2}$ and an inner diameter $ID_{C2}$. Releasing the tensile force from cables 402 after the helical winding process causes (i) the outer diameter of coiled cable assembly 312 to increase from $OD_{C1}$ to $OD_{C2}$ and (ii) the diameter of coil passage 702 to increase from $ID_{C1}$ to $ID_{C2}$. In some embodiments, step 700 (shown in FIG. 7) of removing mandrel 404 from coiled cable assembly 312 may occur after coiled cable assembly 312 transitions from restrained state 800 to expanded state 900.

Figure 12:
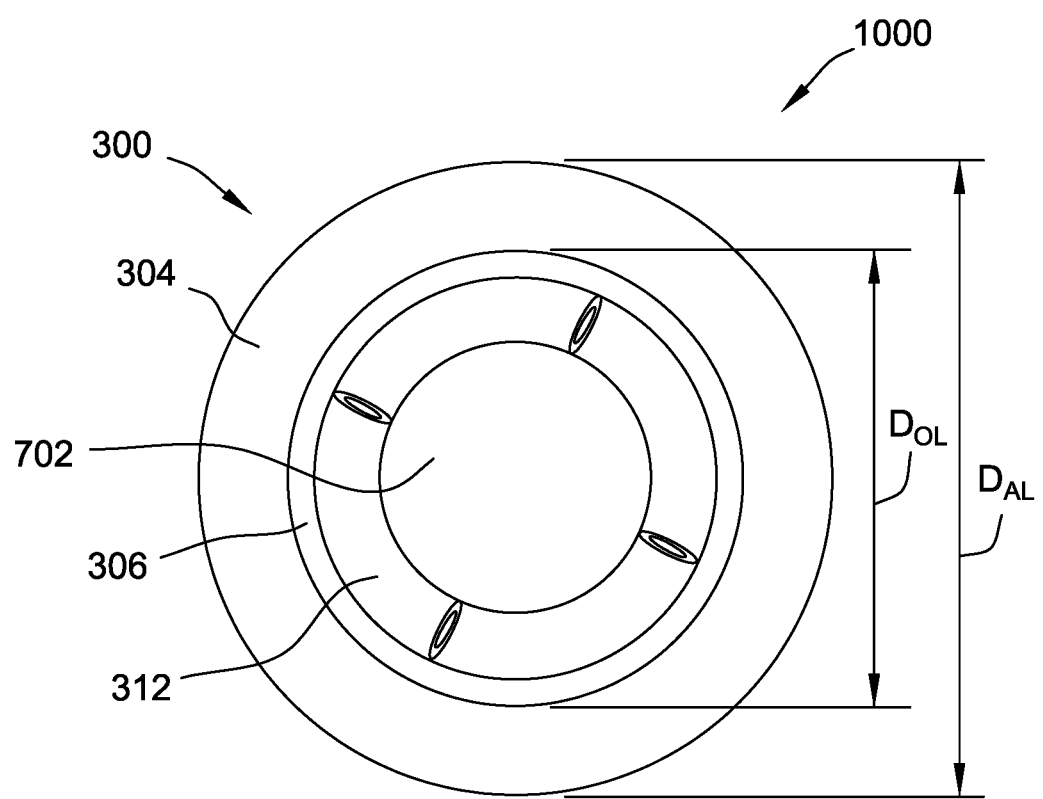
FIG. 12 illustrates another, subsequent step in the exemplary method of forming the assembled lead body of FIG. 3.

As described above, FIGS. 4-11 illustrate forming a free state coiled cable assembly 312 (shown in FIG. 3) separate from the other components of assembled lead body 300. FIG. 12 illustrates another, subsequent step 1000 in the exemplary method of forming assembled lead body 300. FIG. 12 is an end view of outer sheath 304 and coiled cable assembly 312. Step 1000 of the exemplary method of forming assembled lead body 300 includes slidably positioning (e.g., inserting) coiled cable assembly 312 within outer lumen 306 of outer sheath 304. In an example embodiment, the diameter of coiled cable assembly 312 (e.g., $OD_{C2}$, shown in FIG. 11) is smaller than a diameter of outer lumen 306, as shown by $D_{OL}$ (in FIG. 12), such that coiled cable assembly 312 is slidably movable within outer lumen 306 of outer sheath 304.

Figure 13:
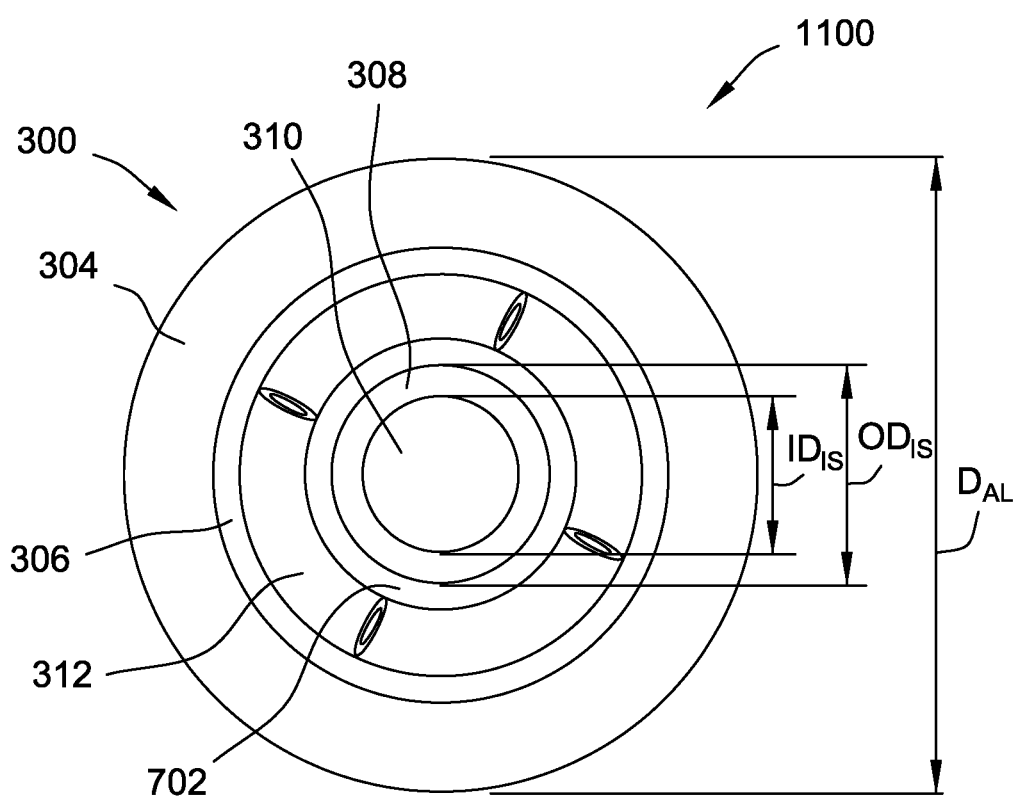
FIG. 13 illustrates another, subsequent step in the exemplary method of forming the assembled lead body of FIG. 3.

FIG. 13 illustrates another, subsequent step 1100 in the exemplary method of forming assembled lead body 300. In particular, FIG. 13 illustrates an end view of assembled lead body 300, including outer sheath 304, coiled cable assembly 312, and inner sheath 308. As shown in FIGS. 12 and 13, assembled lead body 300 has a diameter of $D_{AL}$. Step 1100 includes slidably positioning inner sheath 308 within coil passage 702 of coiled cable assembly 312 to form assembled lead body 300, as shown in FIGS. 3 and 13. Inner sheath 308 has an outer diameter of $OD_{IS}$ and an inner diameter (e.g., diameter of inner lumen 310) of $ID_{IS}$. In an example embodiment, the outer diameter $OD_{IS}$ of inner sheath 308 is smaller than an inner diameter $ID_{C2}$ of coiled cable assembly 312 (e.g., coiled cable assembly 312 in the expanded state, shown in FIG. 11), such that inner sheath 308 is slidably movable within coil passage 702 of coiled cable assembly 312. Outer sheath 304 is formed from a polymer or other heat-shrinkable material. In one embodiment, outer sheath 304 may be formed of a thermoplastic polycarbonate urethane or other insulative material. Inner sheath 308 is formed of a polymer or other material that will bond to coiled cable assembly 312 during a reflow process, as described below.

Figure 14:
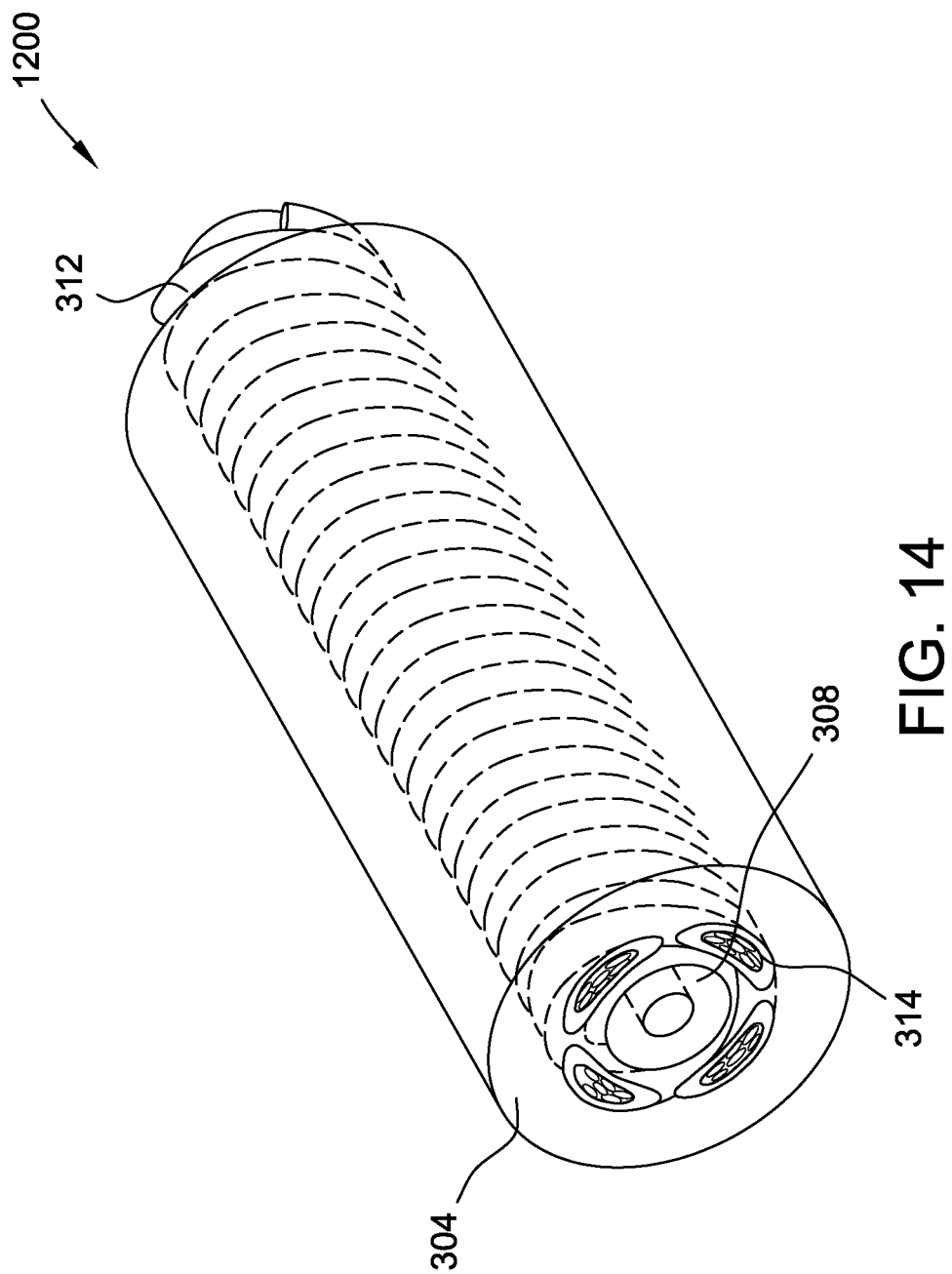
FIG. 14 is a perspective view of an exemplary reflowed lead body suitable for use in the system shown in FIG. 1.
Figure 15:
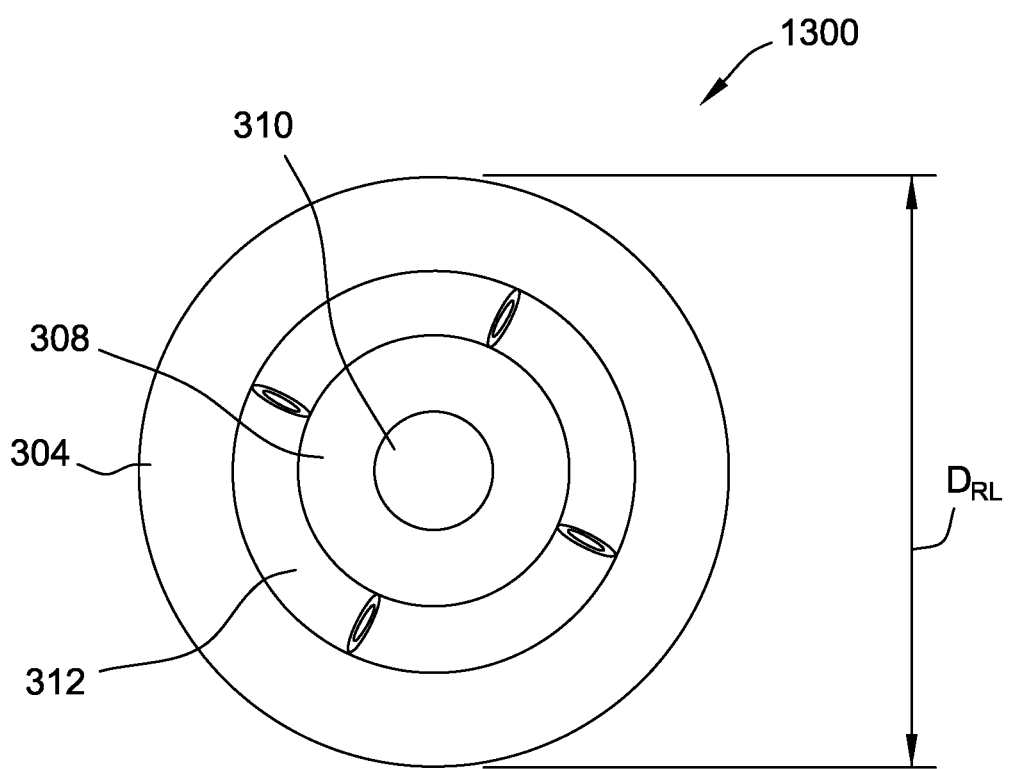
FIG. 15 is a cross section of the exemplary reflowed lead body of FIG. 14.

FIG. 14 illustrates a perspective view of an exemplary reflowed lead body 1200 suitable for use in the system shown in FIG. 1. FIG. 15 illustrates a cross section 1300 of the exemplary reflowed lead body 1200 shown in FIG. 14. With reference to FIGS. 14 and 15, a reflow process is applied to assembled lead body 300 (shown in FIG. 3) to form reflowed lead body 1200. The reflow process includes heating and reflowing assembled lead body 300. Outer sheath 304 is heated and melted to substantially fill and remove any voids or bubbles within lead body 300 and to create a homogenous lead body. In particular, the reflow process causes outer sheath 304 to melt and flow into any gaps along outer lumen 306 (shown in FIG. 13). Inner sheath 308 similarly melts and fuses to coiled cable assembly 312. In some embodiments, electrical insulation of coiled cable assembly 312 may also melt and fuse to outer sheath 304 and/or inner sheath 308 during the reflow process. In an exemplary embodiment, coiled cable assembly 312 is configured to maintain its size and shape (e.g., diameters $OD_{C2}$ and $ID_{C2}$, shown in FIG. 11) during the reflow process. The size and shape of the coiled cable assembly 312 remain unchanged during and after the reflow process. Specifically, when heat is applied to outer sheath 304, the heat does not cause coiled cable assembly 312 to unwind and grow out of outer sheath 304 due to pent up energy stored within coiled cable assembly 312. In the illustrated embodiment, reflowed lead body 1200 has a diameter of $D_{RL}$. The reflow process causes outer sheath 304 to shrink, thereby causing the diameter of assembled lead body 300, $D_{AL}$ (shown in FIGS. 13 and 14) to shrink to a diameter of $D_{RL}$. Accordingly, the diameter $D_{RL}$ of reflowed lead body 1200 is smaller than the diameter $D_{AL}$ of assembled lead body 300. Thus, a size of reflowed lead body 1200 is generally smaller than a size of assembled lead body 300.

Figure 16:
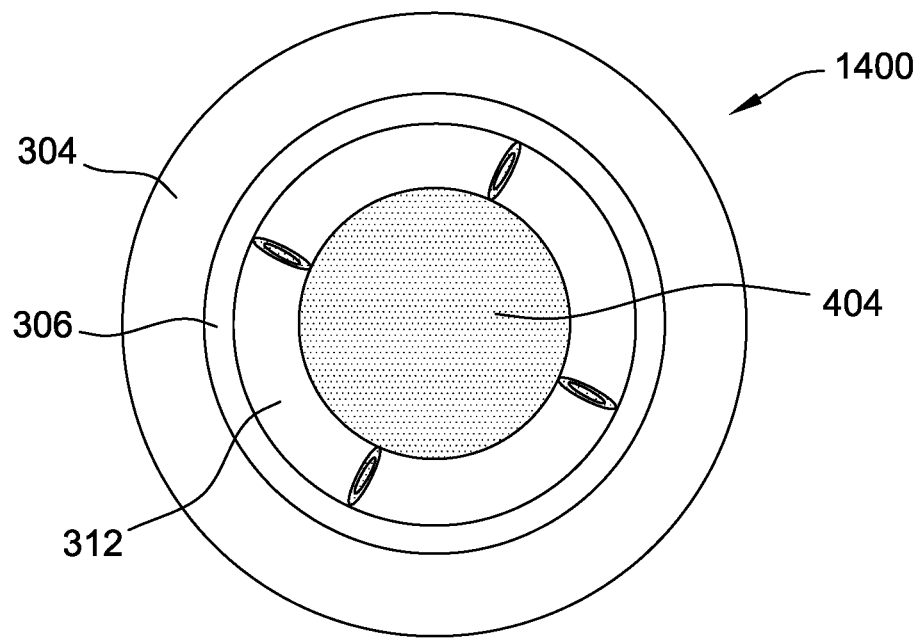
FIG. 16 illustrates a step in an alternative method of forming the assembled lead body of FIG. 3.
Figure 17:
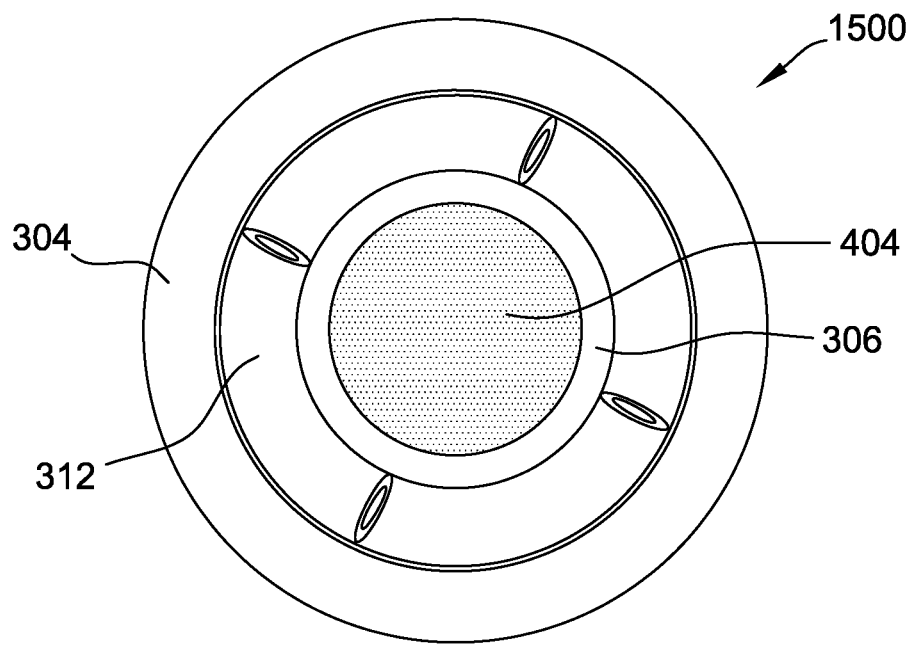
FIG. 17 illustrates another, subsequent step in the alternative method of forming the assembled lead body of FIG. 3.

FIGS. 16-19 illustrate steps 1400-1700 in an alternative method of forming assembled lead body 300 (shown in FIG. 3). In particular, FIGS. 16 and 17 illustrate an end view of outer sheath 304, coiled cable assembly 312, and mandrel 404. After winding cables 402 (shown in FIG. 4) about mandrel 404 to form coiled cable assembly 312, step 1400 of the alternative method includes positioning (e.g., inserting) both the wound coiled cable assembly 312 and mandrel 404 within outer lumen 306 of outer sheath 304 while cables 402 are held under tension. Step 1500 includes releasing the tensile force applied to cables 402 after coiled cable assembly 312 and mandrel 404 are positioned within outer lumen 306 to enable coiled cable assembly 312 to expand within outer lumen 306 and release stored mechanical energy, as illustrated in FIG. 17.

Figure 18:
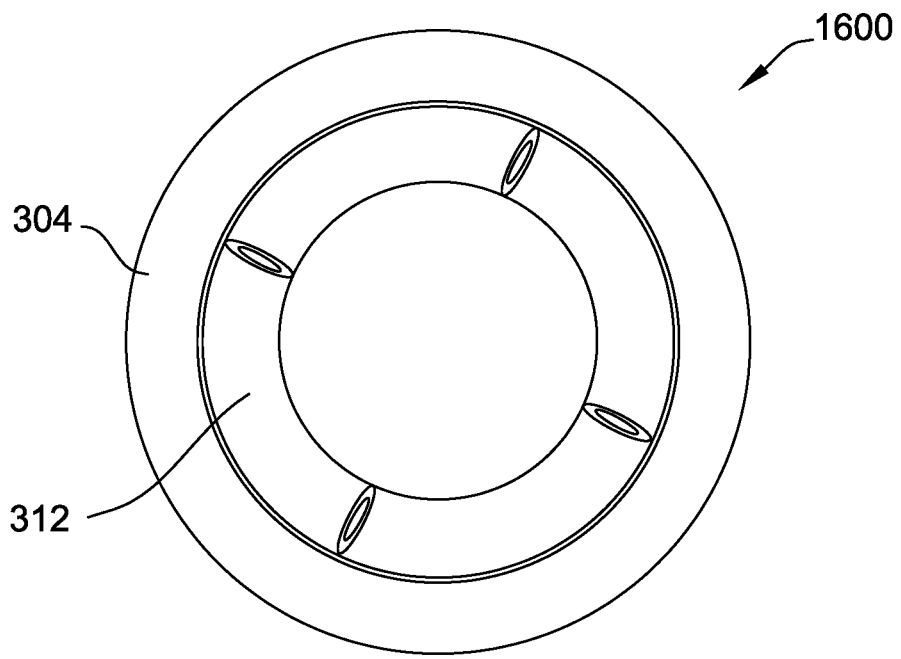
FIG. 18 illustrates another, subsequent step in the alternative method of forming the assembled lead body of FIG. 3.
Figure 19:
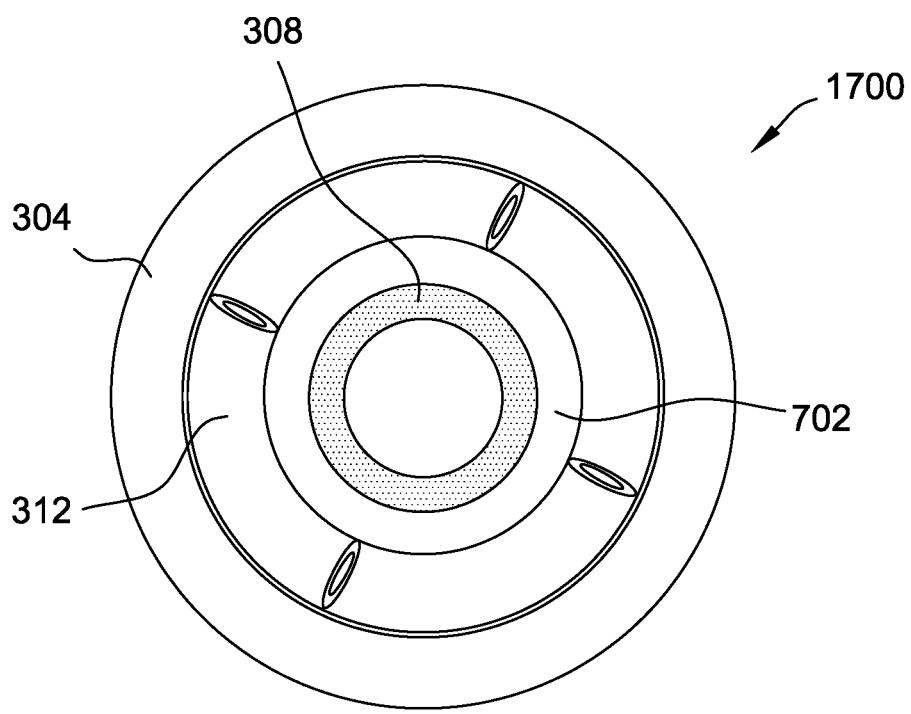
FIG. 19 illustrates another, subsequent step in the alternative method of forming the assembled lead body of FIG. 3.

As shown in FIG. 18, step 1600 includes removing mandrel 404 from outer lumen 306 after coiled cable assembly 312 is allowed to expand. Step 1700, shown in FIG. 19, includes slidably positioning inner sheath 308 within coil passage 702 of coiled cable assembly 312 to form lead body 300 after the mandrel 4040 is removed. In the method illustrated in FIGS. 16-19, the diameter of outer lumen 306 ($D_{OL}$, shown in FIG. 12) is sized based on an outer diameter of coiled cable assembly 312 in the expanded or relaxed state. More specifically, the diameter of outer lumen 306 is sized to enable coiled cable assembly 312 to fully expand and release stored mechanical energy such that coiled cable assembly 312 is in a relaxed state. Moreover, because coiled cable assembly 312 is positioned within outer lumen 306 while in a reduced-diameter state in this embodiment, there is little or no interference between coiled cable assembly 312 and outer sheath 304. As a result, the diameter of outer lumen 306 can be sized approximately equal or just slightly larger than the outer diameter of coiled cable assembly 312 in the expanded state, thereby reducing the gap between coiled cable assembly 312 and outer sheath 304 after the tensile force applied to cables 402 is released. Accordingly, the method illustrated in FIGS. 16-19 can provide a relatively compact assembled lead body, thereby reducing or eliminating the need to perform a subsequent reflow step.

In one embodiment, coiled cable assembly 312 is terminated with contacts (e.g., terminals) and electrodes. In particular, insulative material is removed at or about the proximal and distal ends of the conductive wires of coiled cable assembly 312. Terminals and electrodes are positioned relative to the exposed conductive wires. The proximal and distal ends of each exposed conductive wire are electrically coupled to a respective electrode and terminal. Each exposed conductive wire may be joined to an electrode and terminal in a manner that facilitates a transfer of electrical energy, such as, for example, by resistance welding or laser welding.

FIG. 20 is a flow diagram of an exemplary method 2000 of forming a lead body for use in a stimulation lead. Method 2000 includes helically winding 2002 at least one cable (e.g., cables 402) including a plurality of conductive wires about a mandrel (e.g., mandrel 404) to form a coiled cable assembly (e.g., coiled cable assembly 312) as depicted, for example, in FIGS. 4-6. The coiled cable assembly is in a first, restrained state following step 2002. Helically winding 2002 at least one cable includes applying a tensile force to the at least one cable as the at least one cable is wound about the mandrel. Method 2000 also includes removing 2004 the mandrel from the coiled cable assembly subsequent to the at least one cable being helically wound about the mandrel. Removing 2004 the mandrel from the coiled cable assembly can include, for example and without limitation, slidably removing the mandrel from the coiled cable assembly. In some embodiments, the method 2000 may also include applying a coating to the mandrel, such as a PTFE coating, prior to the at least one cable being helically wound about the mandrel to facilitate removal of the mandrel from the coiled cable assembly. Method 2000 also includes positioning 2006 (e.g., inserting) the coiled cable assembly within an outer lumen of an outer sheath (e.g., outer sheath 304), and releasing 2008 the tensile force from the at least one cable to allow the coiled cable assembly to release stored mechanical energy and transition from the restrained state to a second, relaxed state in which the coiled cable assembly is substantially free of stored mechanical energy. The tensile force applied to the at least one cable may be released 2008 prior to or after the coiled cable assembly being positioned 2006 within the outer lumen of the outer sheath. Method 2000 further includes positioning 2010 (e.g., inserting) an inner sheath (e.g., inner sheath 308) within a coil passage (e.g., coil passage 702) of the coiled cable assembly to form an assembled lead body, and subjecting 2012 the lead body to a reflow process by applying heat to the lead body. The reflow process causes the outer and inner sheaths to at least partially melt and fuse to the coiled cable assembly, and flow into or fill gaps between the coiled cable assembly and the outer and inner lumens.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of forming a stimulation lead, the method comprising:
    forming an implantable lead body, wherein forming the implantable lead body comprises:
    helically winding at least one cable about a mandrel to form a coiled cable assembly in a first, restrained state, wherein helically winding the at least one cable includes applying a tensile force to the at least one cable as the at least one cable is wound about the mandrel;
    restraining a first end of the at least one cable and a second end of the at least one cable, such that a length of the at least one cable defined between the first end and the second end remains fixed, and the coiled cable assembly remains in the restrained state;
    removing the mandrel from the coiled cable assembly while still keeping the first and second ends of the at least one cable restrained, wherein the length of the at least one cable defined between the first and second ends remains the same prior to, during, and immediately after removal of the mandrel, thereby maintaining application of the same tensile force on the at least one cable;
    releasing the tensile force from the at least one cable after the removal of the mandrel to allow the coiled cable assembly to release stored mechanical energy and transition from the restrained state to a second, relaxed state in which the coiled cable assembly is substantially free of stored mechanical energy; and
    subjecting the lead body to a reflow process by applying heat to the lead body, wherein the tensile force is released prior to the lead body being subjected to the reflow process.

2. The method of claim 1, wherein in the first, restrained state, the coiled cable assembly has stored mechanical energy resulting from helically winding the at least one cable about the mandrel.

3. The method of claim 1, wherein an inner diameter of the coiled cable assembly in the first state is smaller than the inner diameter of the coiled cable assembly in the second state.

4. The method of claim 1, wherein the coiled cable assembly extends from a proximal end of the lead body to a distal end of the lead body, and wherein the method further comprises:
   providing a plurality of terminals at the proximal end of the lead body; and
   providing a plurality of electrodes at the distal end of the lead body.

5. The method of claim 4 further comprising electrically coupling each of the plurality of terminals to at least one of the plurality of electrodes through the coiled cable assembly.

6. The method of claim 1, wherein forming the implantable lead body further comprises positioning the coiled cable assembly within a lumen of an outer sheath.

7. The method of claim 6 wherein positioning the coiled cable assembly within a lumen of an outer sheath includes positioning the coiled cable assembly within the lumen of the outer sheath prior to releasing the tensile force from the at least one cable.

8. The method of claim 6, wherein the outer sheath is constructed of a flexible polymer material.

9. The method of claim 6, wherein subjecting the lead body to a reflow process comprises applying heat to the outer sheath.

10. The method of claim 9, wherein subjecting the lead body to a reflow process causes a diameter of the lead body to decrease.

11. The method of claim 9, wherein a size of the coiled cable assembly remains unchanged following the reflow process.

12. The method of claim 1, wherein forming the implantable lead body further comprises positioning an inner sheath within a central elongate passage defined by the coiled cable assembly.

13. The method of claim 1, wherein helically winding the at least one cable comprises helically winding the at least one cable to form a plurality of concentric loops in the coiled cable assembly, wherein helically winding the at least one cable comprises winding the at least one cable about the mandrel such that each loop of the plurality of concentric loops is in contact with adjacent loops of the plurality of concentric loops.

14. The method of claim 1, wherein helically winding the at least one cable comprises helically winding the at least one cable to form a plurality of concentric loops in the coiled cable assembly, wherein helically winding the at least one cable comprises winding the at least one cable about the mandrel such that the plurality of concentric loops is arranged in groups of loops, wherein each group of loops is spaced apart from adjacent groups of loops.

* * * * *